United States Patent [19]

Hayashi et al.

[11] Patent Number: 4,870,291

[45] Date of Patent: Sep. 26, 1989

[54] SPLICE INSPECTION METHOD AND APPARATUS USING LIGHT INCLINED AT A PRESCRIBED ANGLE

[75] Inventors: Youichi Hayashi; Kazuo Kubota; Masaaki Sakaguchi, all of Kanagawa, Japan

[73] Assignee: Fuji Photo Film Co., Ltd., Kanagawa, Japan

[21] Appl. No.: 293,740

[22] Filed: Jan. 4, 1989

[30] Foreign Application Priority Data

Feb. 19, 1988 [JP] Japan .................. 63-37005

[51] Int. Cl.$^4$ .............................................. G06K 7/10
[52] U.S. Cl. ............................ 250/570; 250/223 R; 356/429
[58] Field of Search ............... 250/223 R, 561, 570, 250/571; 356/237–239, 429–431

[56] References Cited

U.S. PATENT DOCUMENTS

| | | | |
|---|---|---|---|
| 3,856,414 | 12/1974 | Menary | 250/570 |
| 4,237,378 | 12/1980 | Jones | 250/223 R |
| 4,286,149 | 8/1981 | Ben-Nathan et al. | 250/223 R |
| 4,297,585 | 10/1981 | Puschmann | 250/570 |
| 4,525,630 | 6/1985 | Chapman | 250/572 |
| 4,611,907 | 9/1986 | Inatsuki | 250/570 |
| 4,652,124 | 3/1987 | Bowen et al. | 250/570 |
| 4,687,321 | 8/1987 | Itoh | 250/570 |
| 4,687,943 | 8/1987 | Bowen et al. | 250/570 |

*Primary Examiner*—David C. Nelms
*Assistant Examiner*—Stephone B. Allen
*Attorney, Agent, or Firm*—Sughrue, Mion, Zinn, Macpeak and Seas

[57] ABSTRACT

A method for inspecting a tape splice for defects in which the splice region between two sheets is irradiated with a light beam, the tapes are longitudinally conveyed relative to the light beam, a one-dimensional light detector means receives the portion of the light beam transmitted or reflected by a linear region of the sheets inclined at a prescribed angle to the transverse direction of the sheets, and the presence/absence of a splice defect is discriminated from change or lack of change in the quantity of light received by the light detector means; and an apparatus for carrying out this method.

16 Claims, 2 Drawing Sheets

SPLICE INSPECTION METHOD AND APPARATUS USING LIGHT INCLINED AT A PRESCRIBED ANGLE

BACKGROUND OF THE INVENTION

1. Field of the Invention

The present invention relates to a method and an apparatus for inspecting the condition of a splice at the portion of an elongate sheet such as a magnetic tape where two lengths of the sheet or tape are connected together and more particularly to a splice inspection method and apparatus suitable for use in the case of, for example, splicing a magnetic tape and a leader tape by means of a splicing tape, for the purpose of inspecting for transverse displacement between the magnetic and leader tapes, overlapping of the tapes, separation between the ends of the tapes and the like.

2. Description of the Prior Art

In the production of audio and video tape cassettes and the like, a leader tape (or trailer tape) is spliced to a magnetic tape by use of a splicing tape. Up to now, determination of whether any transverse displacement, overlapping or separation existed between the two tapes at the splice was left entirely up to visual inspection by the operator.

When visual inspection is relied on, however, there are likely to arise differences in judgment between operators and a tired operator may overlook a faulty product completely. These and other problems make it difficult to maintain a consistent product quality. Moreover, the need to use an operator increases personnel costs, which are reflected in the cost of the product, while the inclusion in the production process of a step carried out by a human being slows down the overall production speed.

As one way of overcoming these problems it might be considered to irradiate the splice region of the tape as the tape is moved in its lengthwise direction, receive the light reflected from or transmitted by this region, and automatically judge the quality of the splice condition by comparing the light quantity information obtained in this way with a prescribed reference value. With this method, if a planar sensor such as a CCD (charge-coupled device) should be used as the means for detecting the reflected or transmitted light, it would be possible to judge the quality of the splice with high accuracy by comparing the information pattern obtained from the planar sensor with a prescribed pattern.

Since planar sensors are expensive, however, the use of such a device would increase the product cost. Moreover, for judging quality with respect to a wide range of different splice conditions it would be necessary to employ sophisticated pattern recognition techniques, which would require a complex inspection software program and lengthen the inspection time.

Another method that might be considered is that of disposing a one-dimensional light sensor so that its lengthwise direction coincides with the transverse direction of the tape, detecting transmitted or reflected light from the whole width of the tape, and judging the quality of the splice from changes in the magnitude of the total light quantity detected. With this method the cost of the light sensor would be lower than in the case of using a CCD or the like and the software required would also be simpler.

With such a method, it would be easy to judge the splice quality as regards overlapping of the tape ends (since the quantity of light received would vary with difference in transmittance or angle of reflection) and as regards separation between the tape ends. However, a complex inspection method would be necessary for determining the splice quality as regards alignment/misalignment of the two spliced tapes in their transverse direction since changes in this alignment would not produce changes in the total quantity of transmitted or reflected light. It might in fact become necessary to provide one system (combination of apparatus and software) for detecting the splice quality as regards transverse displacement and a separate system for detecting splice quality as regards other factors. This would increase the overall cost of conducting the inspection and also increase the inspection time.

SUMMARY OF THE INVENTION

It is an object of the present invention to provide a method and an apparatus for splice inspection which are capable of detecting the quality of a splice between two elongate sheets as regards a wide range of quality factors.

It is another object of the present invention to provide such a method and apparatus that are capable of carrying out the detection rapidly and at low cost.

The splice inspection method according to this invention comprises the steps of irradiating the splice region between two elongate sheets with a light beam, longitudinally conveying the sheets relative to the light beam, receiving by means of a one-dimensional light detector the portion of the light beam transmitted or reflected by a linear region of the sheets inclined at a prescribed angle to the transverse direction of the sheets, and discriminating various types of splice defects from changes in the quantity of received light.

The splice inspection apparatus according to this invention comprises means for irradiating the splice region between two elongate sheets with a light beam, means for longitudinally conveying the elongate sheets relative to the light beam, one-dimensional light detector means for detecting the portion of the light beam transmitted or reflected by a linear region of the sheets inclined at a prescribed angle to the transverse direction of the sheets, and means for discriminating the quality of the splice from changes in the quantity of received light.

In the splice inspection method and apparatus according to the present invention, variation in the transmitted or reflected portion of the light beam directed onto the elongate sheets is detected with respect to a linear region that lies at a prescribed angle to the transverse direction of the sheets. Thus the elongate sheets are not inspected in the transverse direction but along an oblique line. This method is used because if the sheets should be inspected along a linear region lying in the transverse direction, it would not be possible to detect any misalignment between the two sheets in the transverse direction at the splice, the reason being that there would be no difference in the length of the transverse linear region on opposite sides of the splice even if the two sheets should be laterally offset from each other. (While it is technically possible to detect transverse misalignment between the sheets even where the inspection is carried out with respect to a linear region lying in the widthwise direction of the sheets, this would require recognition of the detected pattern and comparison with a reference pattern and would thus necessitate expensive software.)

On the other hand, the length of a linear region lying at an angle to the widthwise direction of the sheets will invariably become shorter at the splice if there is any misalignment between the two sheets. Therefore, if the quantity of light from such an oblique linear region is detected, the presence/absence of sheet misalignment can easily be discriminated from variations in the quantity of detected light (i.e. from changes in the quantity obtained by simple integration).

This method of inspecting the elongate sheets along an oblique line also enables discrimination of defective splices caused by overlapping of the ends of the elongate sheets or by the presence of a gap therebetween since, similarly to the case of detecting lateral misalignment, these states also result in changes in the quantity of light transmitted through or reflected from the sheets at the splice region.

It thus becomes possible to discriminate various types of sheet splice defects by a single, simple method using a one-dimensional light detector.

The above an other objects, features and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Figure 2:
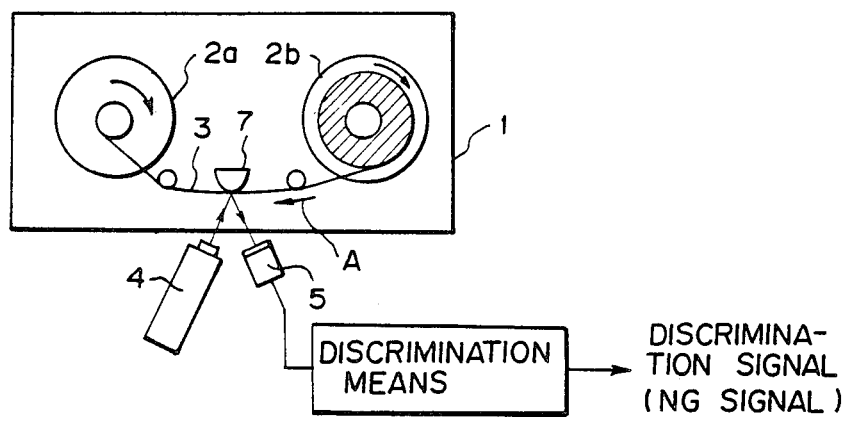
FIG. 2 is an overall plan view of the splice inspection apparatus of FIG. 1.

FIG. 2 is a schematic illustration of an embodiment of the splice inspection apparatus according to this invention. The apparatus comprises a pallet 1 on which are mounted two reels 2a, 2b between which a tape 3 consisting of a leader tape and a magnetic tape spliced thereto runs in the direction of an arrow A, a light irradiating means 4 for irradiating the tape 3 with a parallel beam, a one-dimensional light detector 5 for receiving the portion of the beam from the light irradiating means 4 that is reflected by the tape 3, and a discrimination means 6 which discriminates the quality of the splice between the leader tape and the magnetic tape and outputs an NG (no-good) signal when the splice is found to be defective. Further, on the opposite side of the tape 3 from the light irradiating means 4 and in the vicinity of the position at which the light beam from the light irradiating means 4 impinges on the tape 3, there is provided a backup head 7 which is hollow at the portion opposed to the center region of the sliding tape surface.

Figure 1:
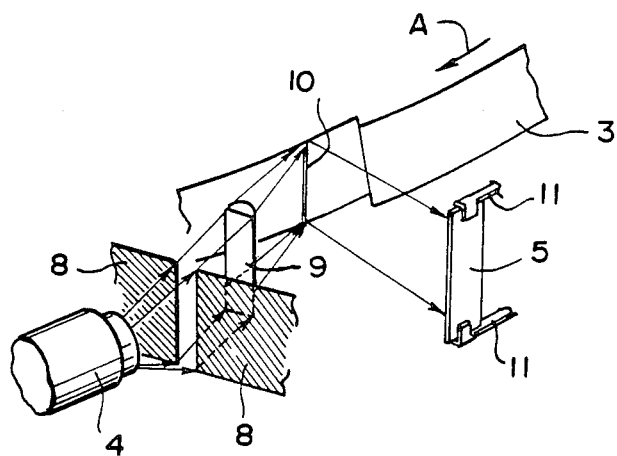
FIG. 1 is a perspective schematic view of one part of a splice inspection apparatus according to an embodiment of the invention.

A slit 8 and a cylindrical lens 9 disposed in front of the light irradiating means 4 forms the light beam into a linear beam which impinges obliquely on the tape 3, as shown in FIG. 1. More precisely, this linear beam irradiates the tape 3 to form thereon a linear region 10 which makes a prescribed angle with respect to the transverse direction of the tape 3 and the portion of the linear beam reflected from this oblique linear region 10 impinges on the one-dimensional light detector 5. The one-dimensional light detector 5 has a long, narrow light-receiving surface and is a simple light detector capable of detecting only the total quantity of received light. It is retained by a light detector retaining means 11 so that the lengthwise direction of its light-receiving surface makes a prescribed angle with the widthwise direction of the tape.

As the tape conveyance means there is used a motor of known type capable of conveying the tape a fixed running speed.

The operation of the aforesaid apparatus for detecting tape splice defects will now be explained.

The reels 2a, 2b are rotated so as to cause the tape 3 to run therebetween at a constant velocity of about 20 cm/sec in the direction of the arrow A. At the same time, the beam from the light irradiating means 4 obliquely irradiates the tape 3. The backup head 7 is disposed to abut on the back of the tape at the portion thereof irradiated by the beam and the one-dimensional light detector 5 is disposed so as to enable it to receive on its light-receiving surface the portion of the beam reflected from the tape. The light quantity information relating to the light reflected from the tape 3 and received by the one-dimensional light detector 5 is input to the discrimination means 6 as a time series electric signal.

The tape 3 under inspection consists of a leader tape and a magnetic tape spliced together by a splicing tape and the leader and magnetic tapes are of approximately the same width. Therefore, if the two tapes are ideally spliced, the upper and lower edges of each will continue smoothly into the upper and lower edges of the other, and their ends will be in contact with each other. However, since it is difficult to precisely position the tapes at the time of splicing them, consistent splicing quality is difficult to obtain and various types of splice defects are apt to occur. These include lateral misalignment, end overlap and end separation. When the degree of such a defect is great, the quality of the product itself will be degraded. It is therefore necessary to ensure that such products are not marketed.

The apparatus according to this embodiment is capable of automatically determining whether or not the degree of tape splice defect is within a preset allowable range and thus of discriminating between good and defective products.

Figure 3:
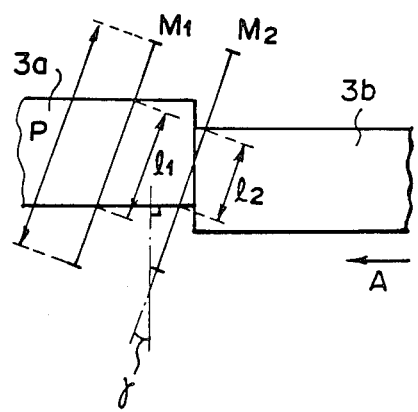
FIG. 3 is a schematic view for explaining the manner in which a tape splice is inspected using the splice inspection apparatus of FIG. 1.

This will be explained with reference to FIG. 3. When the light beam from the light irradiating means 4 impinges on a portion of the tape not in the splice region, such as the region $M_1$, the one-dimensional light detector 5 will receive the light reflected from the linear region $1_1$ constituting a segment of the entire scanned region P. Then when the tape 3 has been conveyed in the direction of the arrow A until the light beam impinges on the splice region between the leader tape 3a and the magnetic tape 3b (region $M_2$), the portion of the entire scanned region P from which light is reflected to the one-dimensional light detector 5 becomes the linear region $1_2$, which is smaller than the linear region $1_1$. As a result, the level of the light quantity signal output by the one-dimensional light detector 5 will decrease at the portion where the tapes are misaligned. The discrimination means 6 constantly compares the level of the light quantity signal with a reference level and when the comparison shows that the output light quantity signal is lower than the reference level, the discrimination means 6 outputs an NG signal indicating that the splice is defective. The angle of inclination $\tau$ of the linear regions $1_1$ and $1_2$ with respect to the transverse direction of the tape is, for example, about 2°. Here it should be noted that in determining the angle $\tau$ it is necessary to give consideration to the angle of inclination that results from snaking of the tape. For example, in a VHS format video tape cassette the width of the tape guides is 3.35 mm larger than the tape width and since the tape guides are spaced at 140 mm intervals, the maximum angle of inclination resulting from snaking of the tape is about 1.4°. Therefore, if the angle $\tau$; is set as the sum of this angle of 1.4° and a margin angle of 0.6°, namely at 2°, the detection will invariably be carried out obliquely. The angle $\tau$ can be set as large as ±30°.

Figure 4:
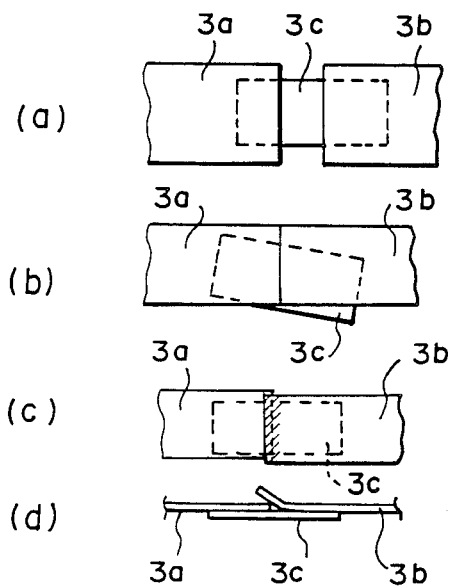
FIG. 4 is a schematic view showing various types of tape splice defects which can be detected with the splice inspection apparatus of FIG. 1.

Further, in the case where the tape splice is defective because of separation between the tape ends as shown in FIG. 4(a), the defect can be detected from a decrease in the level of the light quantity signal in the same manner as when detecting tape misalignment since the splicing tape 3c is narrower than the leader tape 3a and the magnetic tape 3b (by 0.4 mm in the case of a VHS tape).

When the splice is defective because the splicing tape 3c sticks out beyond the edge of the tape as shown in FIG. 4(b), this defect can be detected from an increase in the level of the light quantity signal at the splice region since, contrary to the case of tape misalignment, the length of the linear region irradiated by the light beam becomes longer at this portion so that the quantity of reflected light increases.

When the splice is defective because the ends of the tapes overlap as shown in FIG. 4(c), this defect can be detected from a decrease in the level of the light quantity signal at the splice region caused by the fact that, since one of the tape ends will be bent upward as shown in FIG. 4(d), the reflected portion of the light beam will not be normally received by the one-dimensional light detector 5.

While in the embodiment described above a simple light detector capable of detecting only the total light quantity is used as the one-dimensional light detector 5, the invention is not limited to this arrangement and higher detection accuracy can be realized by alternatively using, for example, a one-dimensional image sensor constituted of a CCD with, say, a capacity of 2048 bits. In this case it becomes possible to carry out pattern analysis separately with respect to each scanning line, and a defective splice can be discriminated by detecting time-course changes in the width of a squarewave corresponding to a region in which the tape is present or by detecting the time shift of the edge of such a squarewave. When this arrangement is used, the discrimination means 6 may be constituted as an 8-bit microcomputer, for example.

Figure 5:
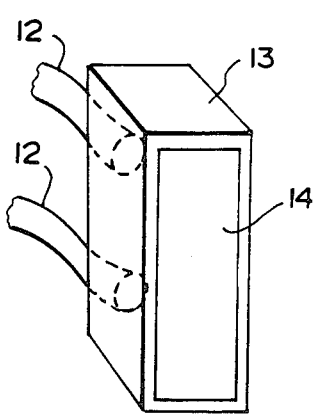
FIG. 5 is a schematic perspective view of one example of a light irradiating means.

Further, if an irradiation unit capable of producing a linear light beam is used for the light irradiating means 4, it becomes unnecessary to provide the slit 8 and the cylindrical lens 9. It is, for example, possible to use an irradiation unit as illustrated in FIG. 5 which consists of a box 13 whose interior walls are finished with white alumite, optical fibers 12 for introducing light into the box 13, and a diffusion plate 14 through which the light is diffused. When this diffused light is used for irradiating the tape, non-uniformity in the received light caused by reflection from a tape with a mirror surface can be reduced, making it possible to prevent erroneous discrimination of small deformations in the tape at the splice region as splice defects.

While the aforesaid embodiment was described with respect to the discrimination of splice defects in audio, video and other kinds of magnetic tapes, the invention is not limited to this kind of inspection and can also be applied without modification to the discrimination of splice defects in polishing tapes, sheet materials, plate materials and the like.

While in the description of the aforesaid embodiment it was stated that the tape is irradiated with a linear beam, the inspection can alternatively be carried out with the same effect by carrying out extremely dense raster scanning of the tape with a beam spot.

Preferably, the discrimination means 6 should be connected with a buzzer which produces an alarm of fixed length each time an NG signal is produced. It is also convenient for identifying defective products to provide a control panel with an LED (light-emitting diode) which lights when an NG signal is produced.

As has been explained in the foregoing, in accordance with the splice inspection method and apparatus according to the present invention, the elongate sheet or tape is inspected on the bias so as to enable simple and quick detection with one and the same apparatus of various types of splice defects, including not only the cases where the sheet or tape ends are overlapped or separated but also the case where the sheet ends are misaligned in their transverse direction. Moreover, since these effects are realized without using an expense planar sensor but by using an inexpensive one-dimensional light detector, the inspection can be carried out at a low cost with the use of simple inspection software that reduces the inspection time.

We claim:

1. In a method of inspecting for defects in a splice between the ends of two elongate sheets of the same width comprising the steps of irradiating a splice region of said sheets with a light beam, longitudinally conveying the sheets relative to the light beam, receiving by means of a one-dimensional light detector the portion of the light beam transmitted or reflected by said sheets, and discriminating the quality of the splice from changes in the quantity of received light, the improved method wherein the light received by said one-dimensional light detector is that reflected or transmitted by a linear region of the sheets inclined at a prescribed angle to the transverse direction of the sheets.

2. A method as defined in claim 1 wherein said prescribed angle is between 2° and 30°.

3. A method as defined in claim 1 wherein said prescribed angle is between minus 2° and minus 30°.

4. A method as defined in claim 1 wherein said sheets are a leader tape and a magnetic tape spliced by a splicing tape.

5. An apparatus for inspecting for defects in a splice between the ends of two elongate sheets of the same width comprising means for irradiating a splice region of said sheets with a light beam, means for longitudinally conveying the elongate sheets relative to the light beam, one-dimensional light detector means for detecting the portion of the light beam transmitted or reflected by a linear region of the sheets inclined at a prescribed angle to the transverse direction of the sheets, and means for discriminating the quality of the splice from changes in the quantity of the light received by said one-dimensional detector means.

6. An apparatus as defined in claim 5 wherein said one-dimensional light detector is capable of detecting only total light quantity.

7. An apparatus as defined in claim 5 wherein said one-dimensional light detector is a charge-coupled device.

8. An apparatus as defined in claim 5 wherein said prescribed angle is between 2° and 30°.

9. An apparatus as defined in claim 5 wherein said prescribed angle is between minus 2° and minus 30°.

10. An apparatus as defined in claim 5 wherein said sheets are a leader tape and a magnetic tape spliced by a splicing tape.

11. An apparatus as defined in claim 5 wherein said discriminating means is an 8-bit microcomputer.

12. An apparatus as defined in claim 5 wherein said irradiating means has a diffusion plate through which the light is passed before impinging on said sheets.

13. An apparatus as defined in claim 5 wherein said irradiating means produces a linear beam.

14. An apparatus as defined in claim 5 wherein said irradiating means a spot beam which raster scans said sheets at high density.

15. An apparatus as defined in claim 5 wherein said discriminating means sounds a buzzer when it discriminates that a splice defect is present.

16. An apparatus as defined in claim 5 wherein said discriminating means lights a light-emitting diode when it discriminates that a splice defect is present.

* * * * *